United States Patent [19]

Jacobi et al.

[11] Patent Number: 5,463,124
[45] Date of Patent: Oct. 31, 1995

[54] PROCESS FOR THE DIASTEREOSELECTIVE REDUCTIVE PINACOL COUPLING OF HOMOCHIRAL α-AMINOALDEHYDES

[75] Inventors: Detlef Jacobi, Ostfildern; Heiner Jendralla; Bernhard Kammermeier, both of Frankfurt am Main, all of Germany

[73] Assignee: Hoechst Aktiengesellschaft, Frankfurt am Main, Germany

[21] Appl. No.: 264,842

[22] Filed: Jun. 22, 1994

Related U.S. Application Data

[63] Continuation of Ser. No. 956,238, Oct. 5, 1992, abandoned.

[30] Foreign Application Priority Data

Oct. 7, 1991 [DE] Germany ............... 41 33 202.4

[51] Int. Cl.$^6$ ............... C07C 237/20; C07C 235/32
[52] U.S. Cl. ............... 564/155; 564/154; 564/153; 564/157; 546/265; 546/146
[58] Field of Search ............... 546/265, 146; 564/152, 154, 155, 158

[56] References Cited

U.S. PATENT DOCUMENTS 5,142,056   8/1992   Kempe et al. ............... 546/265

FOREIGN PATENT DOCUMENTS 2026382   3/1991   Canada .
0402646   12/1990   European Pat. Off. .
WO91/18866   12/1991   WIPO .

OTHER PUBLICATIONS

Kempf et al., J. Med. Chem., vol. 33, pp. 2687–2689 (1990).
Roskamp et al., J. Am. Chem. Society, vol. 109, pp. 3152–3154 (1987).
Roskamp et al., J. Am. Chem. Society, vol. 109, pp. 6551–6553 (1987).
CA116:59556c, Hartung Jack Bardair Jr., Coupling Reactions of Alkynes and Aldehydes promoted by NbCl3.DME.

*Primary Examiner*—Richard L. Raymond
*Assistant Examiner*—Deborah Lambkin
*Attorney, Agent, or Firm*—Finnegan, Henderson, Farabow, Garrett & Dunner

[57] ABSTRACT

Process for the diastereoselective reductive pinacol coupling of homochiral α-aminoaldehydes A process for the preparation of optically pure symmetrical compounds of the formula I

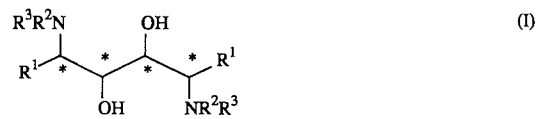

is described in which $R^1$, $R^2$ and $R^3$ are explained in the description, with simultaneous control of the four centers of chirality marked by *.

8 Claims, No Drawings

PROCESS FOR THE DIASTEREOSELECTIVE REDUCTIVE PINACOL COUPLING OF HOMOCHIRAL α-AMINOALDEHYDES

This application is a continuation, of application Ser. No. 07/956,238, filed Oct. 5, 1992, now abandoned.

The invention relates to a process for the preparation of optically pure symmetrical compounds of the formula I

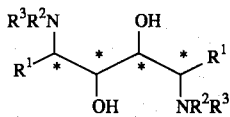
(I)

in which $R^1$, $R^2$ and $R^3$ are explained in greater detail below, with simultaneous control of the four centers of chirality marked by *.

The preparation of compounds of the above type using McMurry reagent [$TiCl_3$/Zn(Cu)] is described in EP-A 0,402,646, which is a counterpart of U.S. Pat. No. 5,142,056 to Kempf et al., and D. J. Kempf et al. [J. Med. Chem. 33, 2687 (1990)]. This reductive coupling method gives mixtures which are difficult to separate. As reported in the publications cited above, the three diastereomers are formed in approximately equal amount and in poor yield.

E. J. Roskamp et al. [J. Am. Chem. Soc. 109, 3152 (1987) and 109, 6551 (1987)] described the fact that synaminoaldehydes can be synthesized diastereoselectively using the niobium (III) or niobium (IV) complexes $NbCl_3$ (DME) and $NbCl_4$ (THF) in the reductive cross-coupling of achiral aldehydes with achiral iminoaldehydes or diastereoselective syn-diamines can be formed in the reductive coupling of iminoaldehydes.

The aim of the present invention is to find a simpler and stereoselective process for the preparation of the abovementioned compounds (I), which does not have the known disadvantages.

The aim is achieved by the process for the preparation of compounds of the formula I

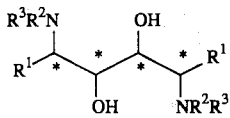
(I)

in which
$R^1$ is a side-chain radical of a natural or unnatural α-amino acid;
$R^2$ and $R^3$ are identical or different and are
a) - hydrogen
b) - a radical of the formula

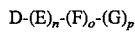
(II)

where E, F and G independently of one another are a natural or unnatural amino acid, aza amino acid or imino acid;

n, o and p independently of one another are 0 or 1;

D is $R^4$ or a radical of the formula III, IV or V

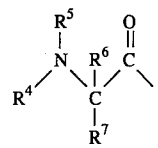
(III)

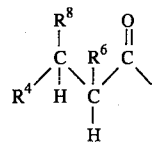
(IV)

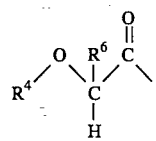
(V)

in which $R^4$ is
$b_1$) - hydrogen,
- carboxyl,
- $(C_1-C_{18})$-alkyl which is optionally monounsaturated or diunsaturated and which is optionally substituted by up to 3 identical or different radicals selected from the group comprising
  - mercapto,
  - hydroxyl,
  - $(C_1-C_7)$-alkoxy,
  - carbamoyl,
  - $(C_1-C_8)$-alkanoyloxy,
  - carboxyl,
  - $(C_1-C_7)$-alkoxycarbonyl,
  - F, Cl, Br or I,
  - amino,
  - amidino which can optionally be substituted by one, two or three $(C_2-C_8)$-alkyl radicals,
  - guanidino which can optionally be substituted by one or two benzyloxycarbonyl radicals or by one, two, three or four $(C_1-C_8)$-alkyl radicals,
  - $(C_1-C_7)$-alkylamino,
  - di-$(C_1-C_7)$-alkylamino,
  - $(C_1-C_6)$-alkoxycarbonylamino,
  - $(C_7-C_{15})$-aralkoxycarbonyl,
  - $(C_7-C_{15})$-aralkoxycarbonylamino,
  - phenyl-$(C_1-C_4)$-alkoxy,
  - 9-fluorenylmethoxycarbonylamino,
  - $(C_1-C_6)$-alkylsulfonyl,
  - $(C_1-C_6)$-alkylsulfinyl,
  - $(C_1-C_6)$-alkylthio,
  - hydroxamino,
  - hydroximino,
  - sulfamoyl,
  - sulfo,
  - carboxamido,
  - formyl,
  - hydrazono,
  - imino,
  - a radical $CONR^9R^{10}$,
  - by up to six hydroxyl or
  - by up to five $(C_1-C_8)$-alkanoyloxy;
- mono-, bi- or tricyclic $(C_3-C_{18})$-cycloalkyl,
- $(C_3-C_{18})$-cycloalkyl-$(C_1-C_6)$-alkyl, where the cycloalkyl moiety is in each case optionally substituted by one or two identical or different radicals selected from the group comprising
  - F, Cl, Br or I,

- carboxyl,
- carbamoyl,
- carboxymethoxy,
- hydroxyl,
- $(C_1-C_7)$-alkoxy,
- $(C_1-C_7)$-alkyl,
- $(C_1-C_7)$-alkoxycarbonyl,
- amino,
- $(C_1-C_6)$-alkylamino-$(C_1-C_6)$-alkyl,
- di-$(C_1-C_6)$-alkylamino-$(C_1-C_6)$-alkyl,
- amidino,
- hydroxamino,
- hydroximino,
- hydrazono,
- imino,
- guanidino,
- $(C_1-C_6)$-alkoxysulfonyl,
- $(C_1-C_6)$-alkoxysulfinyl,
- $(C_1-C_6)$-alkoxycarbonylamino,
- $(C_6-C_6)$-aryl-$(C_1-C_4)$-alkoxycarbonylamino,
- $(C_1-C_7)$-alkylamino,
- di-$(C_1-C_7)$-alkylamino and
- trifluoromethyl;
- $(C_6-C_{14})$-aryl,
- $(C_6-C_{14})$-aryl-$(C_1-C_6)$-alkyl,
- $(C_6-C_{14})$-aryloxy-$(C_1-C_6)$-alkyl or
- $(C_6-C_{14})$-aryl-$(C_3-C_8)$-cycloalkyl, in which the aryl moiety is in each case optionally substituted by one, two or three identical or different radicals selected from the group comprising
  - F, Cl, Br or I,
  - hydroxyl,
  - mono, di- or trihydroxy-$(C_1-C_4)$-alkyl,
  - trifluoromethyl,
  - formyl,
  - carboxamido,
  - mono- or di- $(C_1-C_4)$-alkylaminocarbonyl,
  - nitro,
  - $(C_1-C_7)$-alkoxy,
  - $(C_1-C_7)$-alkyl,
  - $(C_1-C_7)$-alkoxycarbonyl,
  - amino,
  - $(C_1-C_7)$-akylamino,
  - di- $(C_1-C_7)$-alkylamino,
  - carboxyl,
  - carboxymethoxy,
  - amino- $(C_1-C_7)$-alkyl,
  - $(C_1-C_7)$-alkylamino-$(C_1-C_7)$-alkyl,
  - di- $(C_1-C_7)$ -alkylamino- $(C_1-C_7)$-alkyl,
  - $(C_1-C_7)$-alkoxycarbonylmethoxy,
  - carbamoyl,
  - sulfamoyl,
  - $(C_1-C_7)$-alkoxysulfonyl,
  - $(C_1-C_8)$-alkylsulfonyl,
  - sulfo- $(C_1-C_6)$-alkyl,
  - guanidino- $(C_1-C_8)$-alkyl and
  - $(C_1-C_6)$-alkoxycarbonylamino;
- het,
- het- $(C_1-C_6)$-alkyl,
- het- $(C_3-C_8)$-cycloalkyl,
- het- $(C_3-C_8)$-cycloalkyl-$(C_1-C_4)$-alkyl,
- het- $(C_3-C_8)$-cycloalkoxy-$(C_1-C_4)$-alkyl,
- het-thio- $(C_1-C_6)$-alkyl,
- het-thio- $(C_3-C_8)$-cycloalkyl,
- het-thio- $(C_3-C_8)$-cycloalkyl-$(C_1-C_4)$-alkyl, where het in each case is the radical of a 5- to 7-membered monocyclic or 8- to 10- membered bicyclic ring system which can be benzo-fused, aromatic, partly or completely hydrogenated, which as hetero elements can contain one, two, three or four different radicals from the group comprising N, O, S, NO, SO and $SO_2$, which can be substituted by 1 to 6 hydroxyl and which is optionally defined as in the case of $(C_6-C_{14})$-aryl in $b_1$) and/or is mono-, di- or trisubstituted by oxo, or is a radical $NR^6$-$C^{10}$, or $b_2$) - a radical of the formula VI $$R^{4a}- W \quad (VI)$$

in which $R^{4a}$ is defined as $R^4$ in $b_1$) and W is —CO—, —CS—, —O—CO—, —$SO_2$—, —SO—, —S—, —$NHSO_2$—, —NHCO—, —CH(OH)—, —N(OH)— or —CO—V—, where V is a peptide having altogether 1 to 10 amino-, imino- and/or aza amino acids;

or in which $R^4$ together with $R^8$ and the atoms carrying them, form monocyclic or bicyclic, saturated or partially unsaturated ring systems having 5–12 ring members, which, apart from carbon, can also contain 1 sulfur atom which can optionally be oxidized to the sulfoxide or sulfone;

$b_3$) - a glycosyl radical, preferably a glucofuranosyl or glucopyranosyl radical which is derived from naturally occurring aldotetroses, aldopentoses, aldohexoses, ketopentoses, ketohexoses, deoxyaldoses, aminoaldoses and oligosaccharides and their stereoisomers; or $b_4$) - an amino protective group;

$R^5$ is - hydrogen or
- $(C_1-C_8)$-alkyl, or
- together with $R^6$ and the atoms carrying this radical forms mono- or bicyclic, saturated or partially unsaturated ring systems having 5–12 ring members;

$R^6$ is - defined as $R^4$ in $b_1$);
- hydroxyl or $(C_1-C_4)$-alkanoyloxy; or
- together with $R^7$ and the atoms carrying this radical, forms a saturated or partially saturated ring system having 3 to 12 ring members; or
- together with $R^8$ and the atoms carrying this, forms a mono- or bicyclic, saturated or partially saturated ring system having 5–12 ring members which, apart from carbon, can also contain one sulfur atom which can optionally be oxidized to the sulfoxide or sulfone; or can contain one nitrogen atom, where the ring system can optionally be substituted by amino;

$R^7$ is - hydrogen or
- $(C_1-C_6)$-alkyl;

$R^6$ is - hydrogen
- hydroxyl,
- $(C_1-C_4)$-alkanoyloxy or
- $(C_1-C_8)$-alkyl;

$R^9$ and $R^{10}$ are
- hydrogen,
- $(C_1-C_8)$-alkyl which can be substituted by
- amino,
- $(C_1-C_4)$-alkylamino,
- di-$(C_1-C_4)$-alkylamino,
- mercapto,
- carboxyl,
- hydroxyl or
- $(C_1-C_4)$-alkoxy,

- $(C_3-C_7)$-cycloalkyl,
- $(C_1-C_4)$-alkoxycarbonyl,
- $(C_6-C_{14})$-aryl, $(C_6-C_{14})$-aryl-$(C_1-C_4)$-alkoxycarbonyl which can be substituted in the aryl moiety as described in the case of $R^4$,
- het or
- het-$(C_1-C_4)$-alkyl, where het is defined as described in the case of $R^4$, or where $R^9$ and $R^{10}$, together with the nitrogen atom carrying them, form monocyclic or bicyclic, saturated, partially unsaturated or aromatic ring systems which as ring members in addition to carbon also contain 1 or additionally 2 nitrogen atoms, 1 sulfur atom or 1 oxygen atom and can be substituted by $(C_1-C_4)$-alkyl, where in the above compounds of the formula I one or more amide groups (—CONH—) of the main chain can be replaced by —$CH_2NR^{11}$—, —$CH_2S$—, —$CH_2O$—, —$OCH_2$—, —$CH_2CH_2$—, —CH=CH— (cis and trans), —$COCH_2$—, —$CH(OH)CH_2$—, —$CH_2SO$—, —$CH_2SO_2$—, —COO—, —(PCO) $(OR^{12})CH_2$— and —P(O) $(OR^{12})NH$—, or alternatively by an amide group of reverse polarity (—NHCO—);

in which $R^{11}$ and $R^{12}$ independently of one another are
- hydrogen or
- $(C_1-C_4)$-alkyl;

and their enantiomers and physiologically acceptable salts, which comprises treating homochiral α-aminoaldehydes of the formula VII

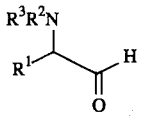
(VII)

in which $R^1$, $R^2$ and $R^3$ are defined as above, with the $NbCl_3$-dimethoxyethane complex [$NbCl_3$ (DME)], simultaneous control over all four centers of chirality existing.

Compounds of the formula I are preferably prepared in which
$R^1$ is a side-chain radical of the α-amino acids Gly, Ala, Val, Leu, Ile, Ser, Thr, Cys, Met, Pro, Lys, Arg, His, Asp, Asn, Glu, Gln, Phe, Tyr, Trp or Cha;
$R^2$ and $R^3$ are identical or different and are
a) - hydrogen
b) - a radical of the formula II
in which o and p=0,
n=0 or 1 and
E is one of the abovementioned a-amino acids,
D is $R^4$ or a radical of the formula III or IV, in which $R^4$ is
$b_1$) - hydrogen
- $(C_1-C_9)$-alkyl which is optionally monounsaturated or diunsaturated and which is optionally substituted by up to 3 identical or different radicals selected from the group comprising
- hydroxyl,
- $(C_1-C_7)$-alkoxy,
- carbamoyl,
- $(C_1-C_8)$-alkanoyloxy,
- $(C_1-C_7)$-alkoxycarbonyl,
- F or Cl,
- amino,
- $(C_1-C_7)$-alkylamino,
- di-$(C_1-C_7)$-alkylamino,
- $(C_1-C_6)$-alkoxycarbonylamino,
- $(C_7-C_{15})$-aralkoxycarbonyl,
- $(C_7-C_{15})$-aralkoxycarbonylamino,
- phenyl-$(C_1-C_4)$-alkoxy,
- 9-fluorenylmethoxycarbonylamino,
- $(C_1-C_6)$-alkylsulfonyl,
- $(C_1-C_6)$-alkylsulfinyl,
- $(C_1-C_6)$-alkylthio,
- $(C_6-C_{14})$-aryl,
- $(C_6-C_{14})$-aryl-$(C_1-C_6)$-alkyl or
- $(C_6-C_{14})$-aryloxy-$(C_1-C_6)$-alkyl, in which the aryl moiety can in each case be optionally substituted by one or two or three identical or different radicals selected from the group of the abovementioned preferred substituents of $(C_1-C_9)$-alkyl,
$b_2$) - a radical of the formula VI, in which
$R^{4a}$ is defined as $R^4$ in $b_1$) and W is —CO—, O—CO—, —$SO_2$—, —SO—, —S—, —NHCO—, —CH(OH)—;
$b_4$) - an amino protective group Fmoc, Z or Boc,
$R^5$ and $R^7$ are hydrogen,
$R^6$ is - defined as $R^4$ and
$R^8$ is - hydrogen,
- hydroxyl,
- $(C_1-C_4)$-alkanoyloxy or
- $(C_1-C_6)$-alkyl.

Preferred compounds of the formula I are further those in which one of the radicals $R^2$ or $R^3$ is hydrogen.

Furthermore, compounds of the formula I with the SRRS-configuration (when aldehydes of the formula VII with the S-configuration are employed) or compounds of the formula I with the RSSR-configuration (when aldehydes of the formula VII with the (R)-configuration are employed) are preferred.

Very particularly preferred compounds of the formula I are those in which
$R^1$ is - a side-chain radical of the α-amino acids Ala, Val, Leu, Ile, Pro, Phe, Cha or Tyr,
$R^2$ and $R^3$ are identical or different and are
a) - hydrogen
b) - a radical of the formula II in which
o and p=0,
n is 0 or 1 and
E is Ala, Val, Leu, Ile, Pro, Phe, Cha or Tyr;
D is $R^4$ or a radical of the formula IV where $R^4$ is
$b_1$) - hydrogen,
- $(C_1-C_4)$-alkyl,
- phenyl or naphthyl,
- phenylmethyl or naphthylmethyl,
$b_2$) - a radical of the formula VI in which $R^{4a}$ is defined as in $b_1$) and W is —CO—, —O—CO—, —$SO_2$—, —SO—, —S—, —NHCO—, —CH(OH)—, or
$b_4$) - an amino protective group Fmoc, Z or Boc,
$R^5$, $R^7$ and $R^8$ are hydrogen, and
$R^6$ is defined as $R^4$ in $b_1$).

Additionally preferred compounds are the example compounds of European Patent Application 0,428,849, which is a counterpart of Canadian Application No. 2,026,382.

Very particularly preferably, compounds of the formula I with the SRRS-configuration are furthermore obtained using aldehydes of the formula VII with the (S)-absolute configuration. This statement only applies under the condition that the group $R^1$ has lower Cahn-Ingold prolog priority than the group —CH(OH)—CH(OH)—.

α-Amino acids can be present, if chiral, in the S- or R-form. They correspond to the formula VIII below

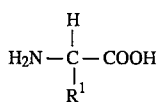
(VIII)

and differ only in the radical $R^1$ of the side chain. By way of example, some natural and unnatural α-amino acids are mentioned below in the three-letter code:

Aad, Abu, ABz, 2ABz, Ach, Acp, Adpd, Ahb, Aib, Ala, Alg, All, Ama, Amt, Ape, Apm, Apr, Arg, Asn, Asp, Asu, Aze, Azi, Bai, Bph, Can, Cha, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, Hyl, Hyp, 3Hyp, Ile, Ise, Iva, Kyn, Lant, Lcn, Leu, Lsg, Lys, Met, Mim, Min, nArg, Nle, Nva, Oly, Orn, Pan, Pec, Pen, Phe, Phg, Pic, Pro, Pse, Pya, Pyr, Pza, Qin, Ros, Sar, Sec, Sem, Ser, Thi, Thr, Thy, Thx, Tia, Tle, Tly, Trp, Trta, Tyr, Val, Nal, Tbg, Npg, Chg, Thia, Cha (see, for example, Houben-Weyl, "Methoden der organischen Chemie" (Methods of Organic Chemistry", volume XV/1 and 2, Stuttgart 1974). If not stated otherwise in individual compounds, the abbreviation of an amino-acid radical without a stereodescripter represents the radical in the L-form, which customarily corresponds to the S-configuration.

An imino acid is generally understood as meaning natural or unnatural amino acids whose amino group is monosubstituted. Compounds which are substituted by $(C_1–C_8)$-alkyl may particulary be mentioned in this connection. Heterocycles of the following group are further suitable:

pyrrolidine-2-carboxylic acid; piperidine-2-carboxylic acid; 1,2,3,4-tetrahydroisoquinoline- 3-carboxylic acid; decahydroisoquinoline-3-carboxylic acid; octahydroindole-2-carboxylic acid; decahydroquinoline-2-carboxylic acid; octahydrocylcopenta[b]pyrrole-2-carboxylic acid; 2-azabicyclo[2.2.2]octane-3-carboxlic acid; 2-azabicyclo[ 2.2.1]heptane-3-carboxylic acid; 2-azabicyclic[ 3.1.0]hexane-3-carboxylic acid; 2-azaspiro[ 4.4]nonane-3-carboxylic acid; 2-azaspiro[ 4.5] decane-3-carboxylic acid; spiro[(bicyclo[2.2.1]heptane)-2,3-pyrrolidine-5-carboxylic acid]; spiro [(bicyclo[2.2.2]octane)- 2,3-pyrrolidine-5-carboxylic acid]; 2-azatricyclo[ 4.3.0.1$^{6,9}$]decane-3-carboxylic acid; decahydrocyclohepta[b]pyrrole-2-carboxylic acid; decahydrocycloocta[b]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3, 3a,4,5,7a-hexahydroindole- 2-carboxylic acid; tetrahydrothiazole-4-carboxylic acid; isoxazolidine-3-carboxylic acid; pyrazolidine-3-carboxylic acid; hydroxyproline- 2-carboxylic acid, all of which can be optionally substituted:

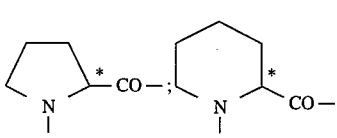

-continued

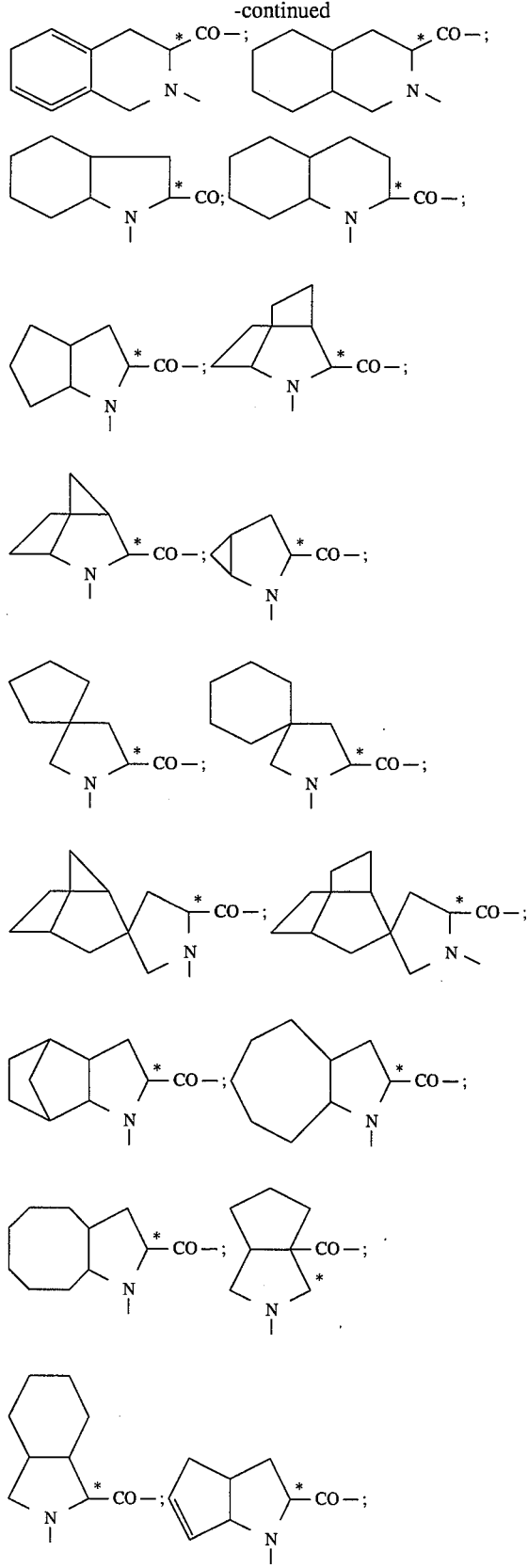

-continued

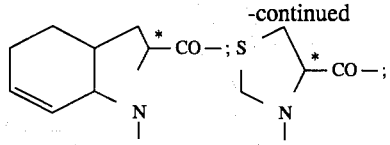
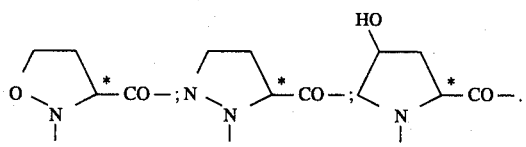

Aza amino acids are derived from natural or unnatural amino acids, the central component —CHR— or —CH$_2$— being replaced by —NR— or —NH—.

An overview of the syntheses, in particular of the unnatural optically active α-amino and imino acids is given by R. M. Williams in "Synthesis of Optically Active α-Aminoacids", Pergamon Press, Oxford 1989.

The nomenclature used in this description follows the general practice with amino acids, i.e. the amino group is on the left and the carboxyl group on the right of each amino acid. The same applies to imino acids and aza amino acids.

Amino protective groups are described in R. Geiger and W. König "The Peptides" Volume 3 "Protection of Functional Groups in Peptide Synthesis", E. G. Gross, J. Meienhofer Edit., Academic Press, New York (1981), in particular pages 7–46. Some are given below by way of example:

| | |
|---|---|
| H—CO— | For |
| CF$_3$—CO— | Pfa |
| 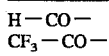 | Pht |
| 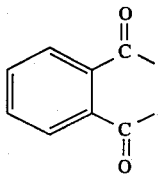 | |
| CH$_3$—CO—CH$_2$—CO— | Aca |
| 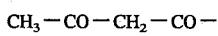 | Maleoyl |
| 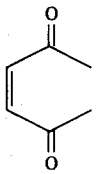 | |
| ClCH$_2$—CO— | Cla |
| 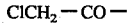 | 2-Nitro-benzoyl |
| 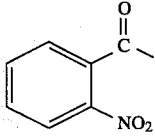 | |

-continued

| | |
|---|---|
| 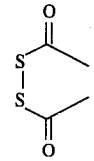 | Dts |
| Cysteic acid | Cys(O$_3$H) |
| 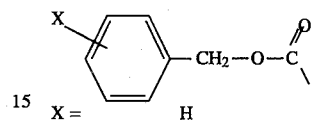 | |
| X = H | Z |
| 2-Cl | 2Cz |
| 4-Cl | 4Cz |
| 4-Br | 4Bz |
| 3-Cl | 3Cz |
| 4-NO$_2$ | 4Nz |
| 4-(C$_6$H$_5$—N=N)— | Paz |
| 4-(CH$_3$O—C$_6$H$_5$—N=N)— | Mpaz |
| 4-CH$_3$ | Mez |
| 4-CH$_3$O | Moz |
| 4-CH$_3$CO—O | 4Acz |
| 4-(HO)$_2$B | Dobz |
| 2-CON(CH$_3$)$_2$ | 2-Dimethyl-aminocarbonyl-Z |
| 2,4-di-Cl | 2,4-Dcz |
| 3,4-di-Cl | 3,4-Dcz |
| 3,5-di-OCH$_3$ | 3,5-Dmoz |
| 2-NO$_2$-4,5-di-OCH$_3$ | 2N-3,5-Dmoz |
| 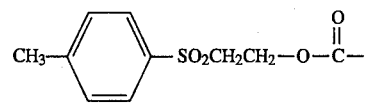 | Tsc |
| CH$_3$—SO$_2$—CH$_2$—CH$_2$—O—CO— | Msc |
| 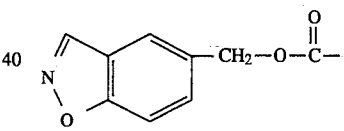 | Bic |
| Ph$_3$P—CH$_2$—CH$_2$—O—CO— | Pec |
| 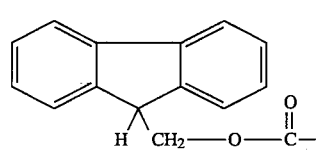 | Fmoc |
| CH$_3$S—CH$_2$—CH$_2$—O—CO— | Mtc |
| 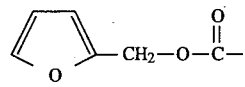 | Foc |
| 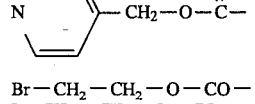 | Inc |
| Br—CH$_2$—CH$_2$—O—CO— | Bec |
| I—CH$_2$—CH$_2$—O—CO— | Iec |

-continued

| | |
|---|---|
| Cl₃C—CH₂—O—CO— | Tcc |
| H₂C=CH—O—CO— | Voc |
| (iPr₂)₂—CH—O—CO— | Dmc |
| 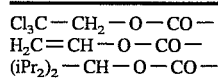 | Cpc |
| 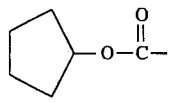 | — |
| 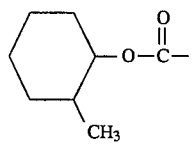 | Ibc |
| Cholesteryl-O—CO— | Coc |
| Ph₂CH—O—CO— | Doc |
| 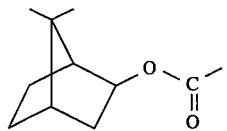 | Dpc |
| (CH₃)₃O—CO— | Boc |
| CH₃—CH₂—C(CH₃)₂—O—CO— | Aoc |
| 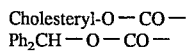 | Adc |
|  | McBoc |
| 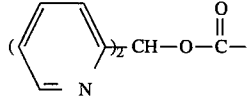 | Mch |
| Ph—C(CH₃)₂—O—CO— | Poc |
| Ph—C₆H₄—C(CH₃)₂—O—CO— | Bpoc |
| 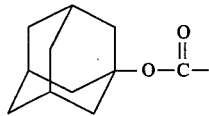 | Ddz |
| 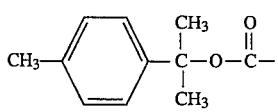 | Mpc |
| 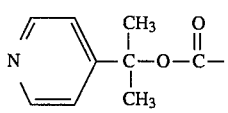 | — |

-continued

| | |
|---|---|
| 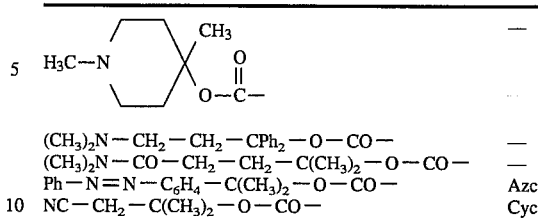 | — |
| (CH₃)₂N—CH₂—CH₂—CPh₂—O—CO— | — |
| (CH₃)₂N—CO—CH₂—CH₂—C(CH₃)₂—O—CO— | — |
| Ph—N=N—C₆H₄—C(CH₃)₂—O—CO— | Azc |
| NC—CH₂—C(CH₃)₂—O—CO— | Cyc |
| 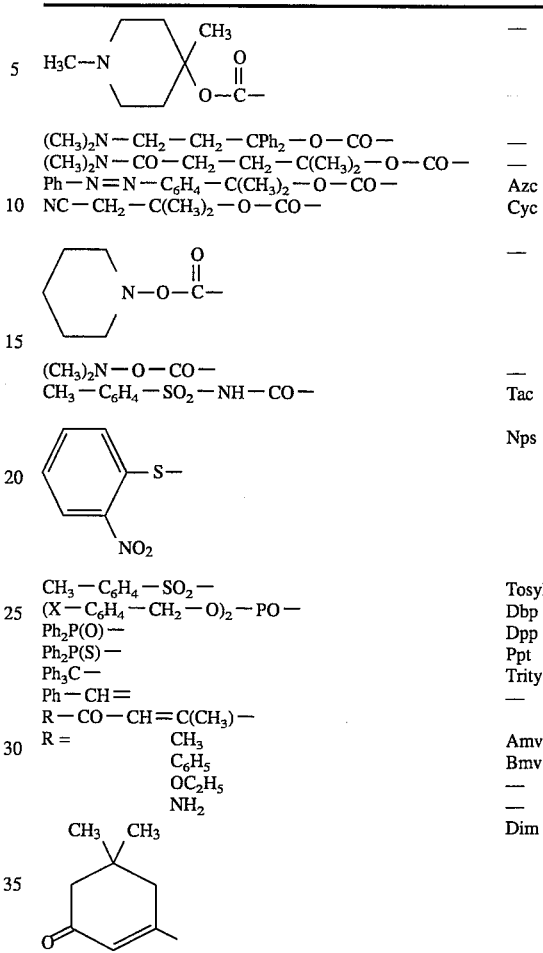 | — |
| (CH₃)₂N—O—CO— | — |
| CH₃—C₆H₄—SO₂—NH—CO— | Tac |
| | Nps |
| CH₃—C₆H₄—SO₂— | Tosyl |
| (X—C₆H₄—CH₂—O)₂—PO— | Dbp |
| Ph₂P(O)— | Dpp |
| Ph₂P(S)— | Ppt |
| Ph₃C— | Trityl |
| Ph—CH= | — |
| R—CO—CH=C(CH₃)— | |
| R = CH₃ | Amv |
| C₆H₅ | Bmv |
| OC₂H₅ | — |
| NH₂ | — |
| | Dim |

Functional groups in the side chains of the amino-, imino- or aza amino acids can be protected, for example, as follows:

a) the guanidino group (for example of arginine) can be protected according to Geiger/König in E. Gross, J. Meienhofer ("The Peptides-Protection of Functional Groups in Peptide Synthesis", Academic Press, New York, 1981), pp. 60–70;

b) the amino nitrogen (for example of lysine) can be protected according to pp. 7–49;

c) the imidazole nitrogen (for example of histidine) can be protected according to pp. 70–80;

d) the pyrazolyl nitrogen (for example of β-3-pyrazolylalanine) can be protected according to pp. 81–82;

e) the indole nitrogen (for example of tryptophan) can be protected according to pp. 82–84;

f) the carboxyl group (for example of aspartic acid) can be protected according to pp. 102–132;

g) the sulfhydryl group (for example of cysteine) can be protected according to pp. 137–169;

h) the hydroxyl group (for example of serine, threonine or tyrosine) can be protected according to pp. 170–201;

i) if R² corresponds to a peptide group, peptide amide nitrogens can be protected, where necessary, according to pp. 52–59.

Glycosyl radicals as described above are derived, in particular, from natural D- or L-monosaccharides occurring in microorganisms, plants, animals or humans, such as ribose (Rib), arabinose (Ara), xylose (Xyl), lyxose (Lyx), allose (All), altrose (Alt), glucose (Glc), mannose (Man), gulose (Gul), idose (Ido), galactose (Gal), talose (Tal), erythrose (Ery), threose (Thr), psicose (Psi), fructose (Fru), sorbose (Sor), tagatose (Tag), xylulose (Xyu), fucose (Fuc), rhamnose (Rha), olivose (Oli), oliose (Olo), mycarose (Myc), rhodosamine (RN), N-acetylglucosamine (GlcNAc), N-acetylgalactosamine (GalNAc), N-acetylmannosamine (ManNAc) or disaccharides such as maltose (Mal), lactose (Lac), cellobiose (Cel), gentiobiose (Gen), N-acetyllactosamine (LacNAc), chitobiose (Chit), β-galactopyranosyl-(1,3)-N-acetylgalactosamine and β-galactopyranosyl-(1-3)- or (1- 4)-N-acetylglucosamine, and their synthetic derivatives, such as 2-deoxy-, 2-amino-, 2-acetamido- or 2-halo-, preferably bromo- and iodo sugars.

Alkyl can be straight-chain or branched. The same applies to radicals derived therefrom, such as, for example, alkoxy, alkylthio, alkylamino, dialkylamino, alkanoyl and aralkyl.

Cycloalkyl is understood as also meaning alkylsubstituted radicals, such as, for example, 4-methylcyclohexyl or 2,3-dimethylcyclopentyl.

$(C_6-C_{14})$-aryl is, for example, phenyl, naphthyl, biphenylyl or fluorenyl; phenyl and naphthyl are preferred. The same applies to radicals derived therefrom, such as, for example, aryloxy, aroyl, aralkyl and aralkoxy. Aralkyl is understood as meaning an unsubstituted or substituted $(C_6-C_{14})$-aryl radical which is linked to $(C_1-C_6)$-alkyl, such as, for example, benzyl, 1- and 2-naphthylmethyl, aralkyl, however, not being restricted to said radicals.

Radicals het within the meaning of the above definition are pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or a benzo-fused, cyclopenta-, cyclohexa- or cyclohepta-fused derivative of these radicals.

These heterocycles can be substituted on a nitrogen atom by oxido; $(C_1-C_7)$-alkyl, for example methyl or ethyl; phenyl; phenyl-$(C_1-C_4)$-alkyl, for example benzyl; and/or on one or more carbon atoms by $(C_1-C_4)$-alkyl, for example methyl; phenyl; phenyl-$(C_1-C_4)$-alkyl, for example benzyl; halogen; hydroxyl; $(C_1-C_4)$-alkoxy, for example methoxy; phenyl-$(C_1-C_4)$-alkoxy, for example benzyloxy; or by oxo and are partially or completely saturated.

Radicals of this type are, for example, 2- or 3-pyrrolyl; phenylpyrrolyl, for example 4- or 5-phenyl-2-pyrrolyl; 2-furyl; 2-thienyl; 4-imidazolyl; methylimidazolyl, for example 1-methyl-2-, -4- or -5-imidazolyl; 1,3-thiazol- 2-yl; 2-, 3- or 4-pyridyl; 2-, 3- or 4-pyridyl N-oxide; 2-pyrazinyl; 2-, 4- or 5-pyrimidinyl; 2-, 3- or 5-indolyl; substituted 2-indolyl, for example 1-methyl-, 5-methyl-, 5-methoxy-, 5-benzyloxy-, 5-chloro- or 4,5-dimethyl- 2-indolyl; 1- benzyl-2- or -3-indolyl; 4,5,6,7-tetrahydro- 2-indolyl; cyclohepta[b]-5-pyrrolyl; 2-, 3- or 4-quinolyl; 1-, 3- or 4-isoquinolyl; 1-oxo-1,2- dihydro- 3-isoquinolyl; 2-quinoxalinyl; 2-benzofuranyl; 2-benzoxazolyl; benzothiazolyl; benz[e]indol-2-yl or β-carbolin- 3-yl.

Partially hydrogenated or completely hydrogenated heterocyclic rings are, for example, dihydropyridinyl, pyrrolidinyl, for example 2-, 3- or 4-N-methylpyrrolidinyl; piperazinyl; morpholino; thiomorpholino; tetrahydrothiophenyl; benzodioxolanyl.

Halogen is fluorine, chlorine, bromine or iodine, in particular fluorine or chlorine.

Salts of compounds of the formula (I) are particularly understood as meaning pharmaceutically utilizable or non-toxic salts.

Such salts are formed, for example, from compounds of the formula (I) which contain acid groups, for example carboxyl, with alkali metals or alkaline earth metals such as, for example, Na, K, Mg and Ca, and with physiologically tolerable organic amines, such as, for example, triethylamine and tris(2-hydroxyethyl)amine.

Compounds of the formula (I) which contain basic groups, for example an amino group or a guanidino group, form salts with inorganic acids, such as, for example, hydrochloric acid, sulfuric acid or phosphoric acid and with organic carboxylic or sulfonic acids, such as, for example, acetic acid, citric acid, benzoic acid, maleic acid, fumaric acid, tartaric acid and p-toluenesulfonic acid.

An embodiment of the process according to the invention comprises dimerizing aldehydes of the formula VII by stereoselective reductive treatment with the niobium (III) complex $NbCl_3(DME)$ in inert solvents in the temperature range from $-78°$ C. to the boiling point of the reaction mixture to give the compounds of the formula I.

The abovementioned niobium complex is isolated from the reaction of $NbCl_5$ with $Bu_3SnH$ (*J. Am. Chem. Soc.* 109, 6551 (1987)); it is additionally commercially available (for example Aldrich Chemie GmbH, Steinheim).

A preferred embodiment for preparing the compounds of the formula I with the abovementioned preferred configurations comprises initially introducing $NbCl_3$ (DME) into a protective gas-flushed apparatus (for example $N_2$ or argon) in inert solvents, such as cyclic or acyclic dialkyl ethers, aromatic or alkyl hydrocarbons, or halogenated hydrocarbons, in particular dichloromethane, di-, tri- or tertachloroethane, toluene or THF at temperatures from $-78°$ C. to the boiling point of the solvent, preferably from $0°$ C. to the boiling point of the solvent, and, relative to the niobium (III) complex, treating with 0.3 to 1.0, preferably 0.7 to 0.9, equivalents of aldehyde of the formula VII and stirring under a protective gas atmosphere (for example $N_2$ or argon) at the respective starting temperature until reaction is complete according to TLC checking. The reaction takes place stereoselectively to a particular extent when using the solvent THF.

For working up, the reaction temperature is preferably adjusted to room temperature and the mixture is treated with the aqueous solution of a complexing agent, preferably 10–30% strength aqueous citric acid or tartrate solution. After separation of the phases, the aqueous phase is extracted with the solvent used in the reaction mixture or as an alternative with a water-immiscible organic solvent, the combined organic phases are washed successively with aqueous base, aqueous acid and water, washed, dried, filtered and evaporated to dryness, after which the crude products is obtained in yields of 20% to 90% of theory. Purification is preferably carried out by crystallization or chromatography on a silica gel column or is unnecessary owing to the adequate purity of the crude product obtained.

The particularly preferred compounds of the formula I in the SRRS-configuration are obtained in particularly high yield from the α-aminoaldehydes of the formula VII with the S-configuration by reaction according to the invention at room temperature to the boiling point of the reaction mixture, in particular at the boiling point of the reaction mixture.

Optically pure α-aminoaldehydes of the formula VII are obtained from amino acids in a simple manner known from the literature, for example as explained in more detail below.

Commercially available or self-synthesized compounds of the formula IX

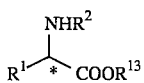 (IX)

in which $R^{13}$ is H, $(C_1-C_4)$-alkyl, $(C_6-C_{14})$-aryl or $(C_6-C_{14})$-aryl-$(C_1-C_6)$-alkyl, in particular methyl, ethyl or benzyl and $R^1$ and $R^2$ are as defined above (Houben Weyl 15/1 and 2, Stuttgart, 1974; V. Teetz, R. Geiger, H. Gaul, Tetrahedron Letters 25/(40), 4479 (1984), A. Pictet, T. Spengler, Chem. Ber. 44, 2030 (1911); R. M. Williams, "Synthesis of Optically Active α-Aminoacids", Pergamon Press, Oxford, 1989) are introduced analogously to methods known from the literature (M. W. Drewes, "The Syntheses and Stereoselective Reactions of α-Aminoaldehydes", Inaugural Dissertation, Department of Chemistry of Philipps University, Marburg/Lahn 1988; and literature cited therein; N. G. Gaylord, "Reduction with Complex Metal Hydrides", Interscience Publishers, NY London, 1956; H. Schenker, Angew. Chemie 73, 81 (1961); C. F. Stanfield, J. E. Parker, P. Kanellis, J. Org. Chem. 46 4797 and 4799 (1981); K. E. Rittle, C. F. Homnick, B. E. Evans, J. Org. Chem. 47, 3016 (1982); K. Haaf, C. Rüchardt, Chem. Ber. 123,635 (1990)) for example with $NaBH_4$ (N. G. Gaylord, see above), $BH_3$·THF (K. E. Rittle, see above) or $LiAlH_4$ (K. Haaf, see above) in inert solvents, or lower alcohols, or alcoholic/aqueous mixtures to give the aminoalcohols of the formula X

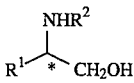 (X)

in which $R^1$ and $R^2$ are as defined above. The compounds of the formula X thus obtained are then reacted by known methods (Houben-Weyl, see above; E. Gross, J. Meienhofer, Ed., "The Peptides - Protection of Functional Groups in Peptide Synthesis", Academic Press, New York, 1981; T. W. Greene, "Protective Groups in Organic Synthesis", John Wiley & Sons, NY Chichester Brisbane Toronto Singapore, 1980; Proceedings of European Peptide Symposium, Platja D'Aro, September 1990) to give the compounds of the formula XI

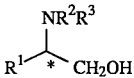 (XI)

with said meanings for $R^1$–$R^3$ and then reacted without racemization with pyridinium dichromate (C. F. Stanfield, see above), $CrO_3$ pyridine (K. E. Rittle, see above), but in particular with $(COCl)_2$ and DMSO and by the Swern Method to give the aldehydes of the formula VII

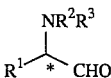 (VII)

in which $R^1$, $R^2$ and $R^3$ are as defined above (K. Omura, A. K. Sharma, D. Swern, J. Org. Chem. 41, 957 (1976); D. Swern, S. L. Huang, A. J. Mancuso, J. Org. Chem. 43, 2480 (1978); A. J. Mancuso, D. Swern, Synthesis, 165 (1981)).

A second variant consists in reacting compounds of the formula IX analogously to the abovementioned syntheses known from the literature to give compounds of the formula XII

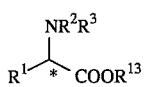 (XII)

in which $R^1$, $R^2$ and $R^3$ and $R^{13}$ are as defined above, and reacting these—after possible prior hydrolysis, without racemization, of an ester of the formula XII where $R^{13} \neq$ H—for example by the method of Weinreb (S. Nahm, S. M. Weinreb, Tetrahedron Letters 22, 3815 (1981)) with N, O-dimethylhydroxylamine to give the compounds of the formula XIII

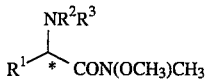 (XIII)

in which $R^1$, $R^2$ and $R^3$ are as defined above. The amides of the formula XIII are converted directly and without racemization, for example by the method of Castro (J. A. Fehrentz, B. Castro, Synthesis, 676 (1983); J. A. Fehrentz, B. Castro, Int. J. Peptide Protein Res. 26,236 (1985)) by reduction with $LiAlH_4$ to said aldehydes of the formula VII.

In a third variant, carboxylic acids of the formula XII ($R^{13}$=H) are derivatized with thionyl chloride or other suitable halogenating agents to the corresponding carbonyl halides of the formula XIV

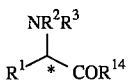 (XIV)

in which $R^1$–$R^3$ corresponds to the above definitions and $R^{14}$ is Cl, Br, I or radicals of mixed carbonic anhydrides, and subsequently reduced without racemization with $H_2$/Pd/$BaSO_4$ to give the aldehydes of the formula VII (analogously to: R. L. Johnson, J. Med. Chem. 25, 605 (1982)). In principle, aldehydes can also be prepared from carboxylic acids and their derivatives using other methods, for example by reaction with simple and complex metal hydrides, metal carbonyl complexes, silanes, alkali metals, formates or photochemically (Houben Weyl 7E3, 418ff, Stuttgart, 1983).

In contrast to the couplings described in Roskamp et al. using niobium complexes (J. Amer. Chem. Soc. 109, 3152 (1987) and 109, 6551 (1987)) reactions without iminoaldehyde components are carried out in the present process, and in addition simultaneous control over four stereocenters is exercized in the present process. When using optically active starting materials, optically active coupling products are obtained in high yield. A further advantage of the process described here is the greater selectivity of the reductant for the activated aldehyde function, which leads to greater compatibility with other functional groups. As described by J. E. McMurry (Chem. Rev. 89, 1513 (1989), in particular Table 2, p. 1515), the McMurry reagent is only partially compatible with functional groups such as, for example, amide, carboxylic acid, ester, ketone and is incompatible with functional groups such as nitro, oxime, sulfoxide, epoxide and 1,2-diol. On the other hand, the niobium complex, for example, is completely compatible with the amide function and other non-activated carboxyl functions also do not react at a significant rate (J. Am. Chem. Soc. 109, 6551 (1987)).

Abbreviations used:
Cha cyclohexylalanine
Chg cyclohexylglycine

DABCO 1,4-diazabicyclo[2.2.2]octane
DME dimethoxyethane
DMF diemethylformamide
DMSO dimethyl sulfoxide
EDTA ethylenediaminetetraacetic acid
HMPA hexamethylphosphoramide
MTB methyl tert-butyl
Nal 1- and 2-naphthylalanine
Npg neopentylglycine
Tbg tert-butylglycine
THF tetrahydrofuran
Thia 2-thienylalanine
TMEDA N,N,N',N'-tetramethylethylenediamine The process according to the invention is further illustrated by the following examples and actual procedure variants are described. These examples and procedure variants do not limit the subject of the invention either with respect to the structural range of the α-aminoaldehydes VII dimerized by diastereoselective reduction in this manner, nor with respect to the process conditions (reagent preparation, physical parameters of reductive dimerization, solvents, reaction time, working up, purification and analysis of the reaction products).

EXAMPLE 1:

N-(tert-Butoxycarbonylamino)-(S)-phenylalanine-N-methoxy-N-methylamide 88.1 g (332 mmol) of (S)-phenylalanine are dissolved in 1.2 l of dichloromethane and treated under a nitrogen atmosphere at a constant internal temperature of 20° C. (cooling by ice-bath) with 268 ml (2.1 mol) of ethylmorpholine and 43.7 g (445 mmol) of N,O-dimethylhydroxylamine hydrochloride. The reaction mixture is cooled to −10° C. and a solution of 252 ml of propanephosphonic anhydride in 250 ml of ethyl acetate is added dropwise. Complete conversion of the reactants is achieved by additional stirring (1 h at 0° C., then 2 h at room temperature). The mixture is washed with 1 of 3 N HCl, 800 ml of saturated, aqueous NaHCO$_3$ solution and 800 ml of saturated, aqueous NaCl solution, and the organic phase is dried over Na$_2$SO$_4$. After evaporating the solvent, 100 g of a colorless oil remain, which can be subjected without further purification to the reduction to give the corresponding aminoaldehyde.

EXAMPLE 2:

N- (tert-Butoxycarbonyl)-(S)-phenylalaninal 4.36 g of lithium aluminum hydride are initially introduced at 0° C. under a nitrogen atmosphere into 875 ml of dry diethyl ether and a solution of 26.9 g of N-(tert-butoxycarbonylamino)-(S)-phenylalanine-N-methoxy-N-methylamide in 73 ml of diethyl ether is added with stirring. The mixture is stirred at 0° C. for 30 min and then treated with 450 ml of 5% strength cold aqueous KHSO$_4$ solution. The phases are separated, and the organic phase is washed successively with 300 ml of 0.5N HCl, 600 ml of saturated aqueous NaHCO$_3$ solution and 600 ml of saturated aqeous NaCl solution, and finally dried over Na$_2$SO$_4$. After evaporation of the solvent, 20.9 g (96.3%) of white crystals remain, which can be employed without further purification for the reductive coupling.

EXAMPLE 3:

(N-(tert-Butoxycarbonylvalinyl)amino)-(S)-phenylalaninal 2.1 ml (25 mmol) of oxalyl chloride are dissolved in 125 ml of dry dichloromethane under an inert gas atmosphere. 2.4 ml (33.4 mmol) of DMSO are added dropwise at −70° C. with stirring and a solution of 5.85 g (16.7 mmol) of N-(tert-butoxycarbonyl)-(S)-valyl-(S)-phenylalaninol in a mixture of 4 ml of DMSO and 30 ml of dichloromethane is slowly added after a waiting time of 15 min. The reaction mixture is additionally stirred at −70° C. for 30 min and 9.4 ml (66.8 mmol) of triethylamine are then added dropwise, the temperature rising to −60° C. After a further 15 min at −60° C. the mixture is hydrolyzed with 200 ml of 15% strength aqueous citric acid and the phases are separated. The organic phase is washed successively in each case with 200 ml of saturated aqueous bicarbonate solution, with water and finally with saturated aqueous sodium chloride solution and dried over sodium sulphate. After evaporating the solvent, 4.4 g of white crystals remain, which are subjected to the dimerization without further purification steps.

General experimental procedure for the reductive coupling:

1.4 eq. of trichloro(dimethoxyethane)niobium (III) are initially introduced into 10 ml of dry solvent under an inert gas atmosphere and treated with 1 eq. of aldehyde in 2 ml of dry solvent and the reaction temperature is adjusted. When the temperature is stable, the reaction conversion is monitored by means of TLC checking. After the reaction has taken place, extraction by shaking at room temperature with aqueous sodium tartrate solution and aqueous citric acid solution, successive washing of the organic phase with aqueous base solution, aqueous acid and water, drying of the organic phase over Na$_2$SO$_4$, filtering off of the drying agent and removal of the solvent yields an oily or solid residue which is optionally purified by chromatography on silica gel and/or by crystallization.

EXAMPLE 4:

N,N'-bis(tert-Butoxycarbonyl)-2S,5S-diamino-1,6-diphenylhexane- 3R,4R-diol

Starting from 2.5 g of N-(tert-butoxycarbonyl)-(S)-phenylalaninal, 1.5 g of crystals of the title compound are obtained analogously to the general procedure (solvent: THF; reaction temperature: reflux).

MS (FAB): 507 (M+Li$^+$), 401, 352,307

EXAMPLE 5:

(2S, 3R, 4R, 5S)-2,5-(N,N'-((tert-Butoxycarbonyl)-(S)-valinyl) amino)-3,4-dihydroxy-1,6-diphenylhexane Starting from 3.5 g of N-(tert-butoxycarbonyl)-(S)-valinyl-phenylalaninal, 1.9 g of oil of the title compound are obtained analogously to the general procedure.

(Solvent: THF; reaction temperature: reflux).

MS (FAB): 705 (M+Li$^+$), 699 (M+H$^+$), 667,605,599.

EXAMPLE 6:1

1,2-Bis [ N-{2(S)-(1,1-dimethylethylsulfonylmethyl)-3-(1-naphthyl)propionyl] -(S)-valyl]-(S)-1, 2, 3, 4-tetrahydroisoquinolin- 3-yl]ethane-1(R),2(R)-diol Starting from 2.5 g of N-[{(S)-2-(1,1-dimethylethylsulfonylmethyl)- 3-(1-naphthyl)propionyl}-(S)-valyl] -(S)-1,2, 3,4-tetrahydroisoquinoline-3-carbaldehyde, 0.8 g of yellowish crystals of the title compound are obtained analogously to the experimental procedure with in situ preparation of the coupling reagent (complexing agent: 1,3-dimethylimidazolidin-2one).

MS (FAB): 1162 (M+Li⁺), 1156 (M+H⁺), 741, 388.

EXAMPLE 7:

N,N'-Bis[{(S)-2-(1,1-diemthylethylsulfonylmethyl)-3-(1-naphthyl)-propionyl} -(S)-valyl]-2(S) ,5(S)-diamino-1,6-diphenylhexane- 3(R),4(R)-diol

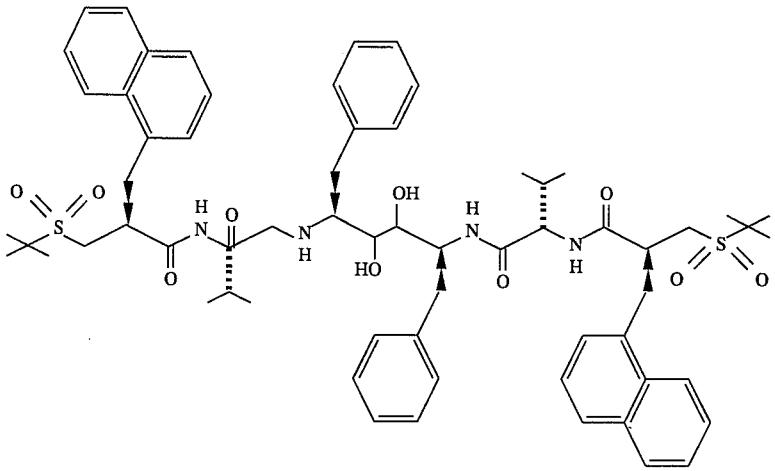

Starting from 2.0 g of N-[{(S)-2-(1,1-dimethylethylsulfonylmethyl)- 3-(1-naphthyl)propionyl}-(S)-valyl] -(S)-phenylalaninal, 0.8 g of crystals of the title compound are obtained analogously to the general procedure.

(Solvent: THF; reaction temperature: reflux).

MS (FAB): 1154 (M+Na⁺), 1132 (M+H⁺), 716, 567.

We claim:

1. A process for the preparation of compounds of the formula I

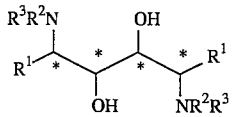  (I)

in which $R^1$ is a side-chain radical of a natural or unnatural α-amino acid;

$R^2$ and $R^3$ are identical or different and are a) - hydrogen b) - a radical of the formula $$D-(E)_n-(F)_o-(G)_p \quad (II)$$

where E, F and G independently of one another are a natural or unnatural amino acid, aza amino acid or imino acid;

n, o and p independently of one another are 0 or 1;

D is $R^4$ or a radical of the formula III, IV or V

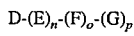  (III)

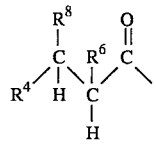  (IV)

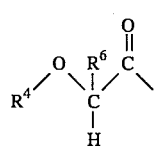  (V)

in which $R^4$ is b₁) - hydrogen,
- carboxyl,
- $(C_1-C_{18})$-alkyl which is optionally monounsaturated or di- unsaturated and which is optionally substituted by up to 3 identical or different radicals selected from the group comprising
  - mercapto,
  - hydroxyl,
  - $(C_1-C_7)$-alkoxy,
  - carbamoyl,
  - $(C_1-C_7)$-alkanoyloxy,
  - carboxyl,
  - $(C_1-C_7)$-alkoxycarbonyl,
  - F, Cl, Br or I,
  - amino,
  - amidino which can optionally be substituted by one, two or three $(C_1-C_8)$-alkyl radicals,
  - guanidino which can optionally be substituted by one or two benzyloxycarbonyl radicals or by one, two, three or four $(C_1-C_8)$-alkyl radicals,
  - $(C_1-C_7)$-alkylamino,
  - di-$(C_1-C_7)$-alkylamino,
  - $(C_1-C_6)$-alkoxycarbonylamino,
  - $(C_7-C_{15})$-aralkoxycarbonyl,
  - $(C_7-C_{15})$-aralkoxycarbonylamino,

- phenyl-$(C_1-C_c)$-alkoxy,
- 9-fluorenylmethoxycarbonylamino,
- $(C_1-C_6)$-alkylsulfonyl,
- $(C_1-C_6)$-alkylsulfinyl,
- $(C_1-C_6)$-alkylthio,
- hydroxamino,
- hydroximino,
- sulfamoyl,
- sulfo,
- carboxamido,
- formyl,
- hydrazono,
- imino,
- a radical $CONR^9R^{10}$,
- by up to six hydroxyl or
- by up to five $(C_1-C_8)$-alkanoyloxy;

- mono-, bi- or tricyclic $(C_3-C_{18})$-cycloalkyl,
- $(C_3-C_{18})$-cycloalkyl-$(C_1-C_6)$-alkyl, where the cycloalkyl moiety is in each case optionally substituted by one or two identical or different radicals selected from the group comprising
  - F, Cl, Br or I,
  - carboxyl,
  - carbamoyl,
  - carboxymethoxy,
  - hydroxyl,
  - $(C_1-C_7)$-alkoxy,
  - $(C_1-C_7)$-alkyl,
  - $(C_1-C_7)$-alkoxycarbonyl,
  - amino,
  - $(C_1-C_6)$-alkylamino-$(C_1-C_6)$-alkyl,
  - di-$(C_1-C_6)$-alkylamino-$(C_1-C_6)$-alkyl,
  - amidino,
  - hydroxamino,
  - hydroximino,
  - hydrazono,
  - imino,
  - guanidino,
  - $(C_1-C_6)$-alkoxysulfonyl,
  - $(C_1-C_6)$-alkoxysulfinyl,
  - $(C_1-C_6)$-alkoxycarbonylamino,
  - $(C_6-C_{12})$-aryl-$(C_1-C_4)$-alkoxycarbonylamino,
  - $(C_1-C_7)$-alkylamino,
  - di-$(C_1-C_7)$-alkylamino and
  - trifluoromethyl;

- $(C_6-C_{14})$-aryl,
- $(C_6-C_{14})$-aryl-$(C_1-C_6)$-alkyl,
- $(C_6-C_{14})$-aryloxy-$(C_1-C_6)$-alkyl or
- $(C_6-C_{14})$-aryl-$(C_3-C_8)$-cycloalkyl, in which the aryl moiety is in each case optionally substituted by one, two or three identical or different radicals selected from the group comprising
  - F, Cl, Br or I,
  - hydroxyl,
  - mono-, di- or trihydroxy-$(C_1-C_4)$-alkyl,
  - trifluoromethyl,
  - formyl,
  - carboxamido,
  - mono- or di-$(C_1-C_4)$-alkylaminocarbonyl,
  - nitro,
  - $(C_1-C_7)$-alkoxy,
  - $(C_1-C_7)$-alkyl,
  - $(C_1-C_7)$-alkoxycarbonyl,
  - amino,
  - $(C_1-C_7)$-akylamino,
  - di-$(C_1-C_7)$-alkylamino,
  - carboxyl,
  - carboxymethoxy,
  - amino-$(C_1-C_7)$-alkyl,
  - $(C_1-C_7)$-alkylamino-$(C_1-C_7)$-alkyl,
  - di-$(C_1-C_7)$-alkylamino-$(C_1-C_7)$-alkyl,
  - $(C_1-C_7)$-alkoxycarbonylmethoxy,
  - carbamoyl,
  - sulfamoyl,
  - $(C_1-C_7)$-alkoxysulfonyl,
  - $(C_1-C_8)$-alkylsulfonyl,
  - sulfo-$(C_1-C_8)$-alkyl,
  - guanidino-$(C_1-C_6)$-alkyl and
  - $(C_1-C_6)$-alkoxycarbonylamino;

- het,
- het-$(C_1-C_6)$-alkyl,
- het-$(C_3-C_8)$-cycloalkyl,
- het-$(C_3-C_8)$-cycloalkyl-$(C_1-C_4)$-alkyl,
- het-$(C_3-C_8)$-cycloalkoxy-$(C_1-C_4)$-alkyl,
- het-thio-$(C_1-C_6)$-alkyl,
- het-thio-$(C_3-C_8)$-cycloalkyl,
- het-thio-$(C_3-C_8)$-cycloalkyl-$(C_1-C_4)$-alkyl, where het in each case is the radical of a 5- to 7-membered monocyclic or 8- to 10-membered bicyclic ring system which can be benzo-fused, aromatic, partly or completely hydrogenated, which as hetero elements can contain one, two, three or four different radicals from the group comprising N, O, S, NO, SO and $SO_2$, which can be substituted by 1 to 6 hydroxyl and which is optionally defined as in the case of $(C_6-C_{14})$-aryl in $b_1$) and/or is mono-, di- or trisubstituted by oxo, or is a radical $NR^9R^{10}$, or $b_2$) - a radical of the formula VI $$R^{4a}-W \quad (VI)$$

in which $R^{4a}$ is defined as $R^4$ in $b_1$) and W is —CO—, —CS—, —O—CO—, —$SO_2$—, —SO—, —S—, —$NHSO_2$—, —NHCO—, —CH(OH)—, —N(OH)— or —CO-V—, where V is a peptide having altogether 1 to 10 amino-, imino- and/or aza amino acids;

or in which $R^4$ together with $R^8$ and the atoms carrying them, form monocyclic or bicyclic, saturated or partially unsaturated ring systems having 5–12 ring members, which, apart from carbon, can also contain 1 sulfur atom which can optionally be oxidized to the sulfoxide or sulfone;

$b_3$) - a glycosyl radical, preferably a glucofuranosyl or glucopyranosyl radical which is derived from naturally occurring aldotetroses, aldopentoses, aldohexoses, ketopentoses, ketohexoses, deoxyaldoses, aminoaldoses and oligosaccharides and their stereoisomers; or $b_4$) - an amino protective group;

$R^5$ is - hydrogen or
- $(C_1-C_8)$-alkyl, or
- together with $R^6$ and the atoms carrying this radical forms mono- or bicyclic, saturated or partially unsaturated ring system having 5–12 ring members;

$R^6$ is - defined as $R^4$ in $b_1$);
- hydroxyl or $(C_1-C_4)$-alkanoyloxy; or
- together with $R^7$ and the atoms carrying this radical, forms a saturated or partially saturated ring system having 3 to 12 ring members; or
- together with $R^8$ and the atoms carrying this, forms a mono- or bicyclic, saturated or partially saturated ring system having 5–12 ring members which, apart from carbon, can also contain one sulfur atom which can optionally be oxidized to the sulfoxide or sulfone; or can contain one nitrogen atom, where the ring system can optionally be substituted by amino;

$R^7$ is - hydrogen or
- $(C_1-C_6)$-alkyl;

$R^8$ is - hydrogen
- hydroxyl,
- $(C_1-C_4)$-alkanoyloxy or
- $(C_1-C_8)$-alkyl;

$R^9$ and $R^{10}$ are
- hydrogen,
- $(C_1-C_8)$-alkyl which can be substituted by
- amino,
- $(C_1-C_4)$-alkylamino,
- di-$(C_1-C_4)$-alkylamino,
- mercapto,
- carboxyl,
- hydroxyl or
- $(C_1-C_4)$-alkoxy,
- $(C_3-C_7)$-cycloalkyl,
- $(C_1-C_4)$-alkoxycarbonyl,
- $(C_6-C_{14})$-aryl, $(C_6-C_{14})$-aryl-$(C_1-C_4)$-alkoxycarbonyl which can be substituted in the aryl moiety as described in the case of $R^4$,
- het or
- het-$(C_1-C_4)$-alkyl, where het is defined as described in the case of $R^4$,
or where $R^9$ and $R^{10}$, together with the nitrogen atom carrying them, form monocyclic or bicyclic, saturated, partially unsaturated or aromatic ring systems which as ring members in addition to carbon also contain 1 or additionally 2 nitrogen atoms, 1 sulfur atom or 1 oxygen atom and can be substituted by $(C_1-C_4)$-alkyl, where in the above compounds of the formula I one or more amide groups (—CONH—) of the main chain can be replaced by —CH$_2$NR$^{11}$, —CH$_2$S—, —CH$_2$O—, —OCH$_2$—, —CH$_2$CH$_2$—, —CH=CH—( cis and trans ), —COCH$_2$—, —CH(OH)CH$_2$—, —CH$_2$SO—, —CH$_2$SO$_2$—, —COO—, —P(O)(OR$^{12}$)CH$_2$— and —P(O)(OR$^{12}$)NH—, or alternatively by an amide group of reverse polarity (—NHCO—);

in which $R^{11}$ and $R^2$ independently of one another are
- hydrogen or
- $(C_1-C_4)$-alkyl;

and their enantiomers and physiologically acceptable salts, which comprises treating homochiral α-aminoaldehydes of the formula VII

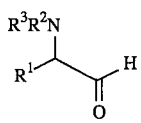
(VII)

in which $R^1$ $R^2$ and $R^3$ are defined as above, with the NbCl$_3$-dimethoxyethane complex [NbCl$_3$ (DME)], and simultaneously controlling over all four centers of chirality.

2. The process for the preparation of compounds of the formula I as claimed in claim 1, wherein $R^1$ is a side-chain radical of the α-amino acids Gly, Ala, Val, Leu, Ile, Ser, Thr, Cys, Met, Pro, Lys, Arg, His, Asp, Asn, Glu, Gln, Phe, Tyr, Trp or Cha;

$R^2$ and $R^3$ are identical or different and are
a) - hydrogen
b) - a radical of the formula II
in which o and p=0,
n=0 or 1 and
E is one of the abovementioned α-amino acids,
D is $R^4$ or a radical of the formula III or IV, in which $R^4$ is b$_1$) - hydrogen
- $(C_1-C_9)$-alkyl which is optionally monounsaturated or diunsaturated and which is optionally substituted by up to 3 identical or different radicals selected from the group comprising
- hydroxyl,
- $(C_1-C_7)$-alkoxy,
- carbamoyl,
- $(C_1-C_8)$-alkanoyloxy,
- $(C_1-C_7)$-alkoxycarbonyl,
- F or Cl,
- amino,
- $(C_1-C_7)$-alkylamino,
- di- $(C_1-C_7)$-alkylamino,
- $(C_1-C_6)$-alkoxycarbonylamino,
- $(C_7-C_{15})$-aralkoxycarbonyl,
- $(C_7-C_{15})$-aralkoxycarbonylamino,
- phenyl-$(C_1-C_4)$-alkoxy,
- 9-fluorenylmethoxycarbonylamino,
- $(C_1-C_6)$-alkylsulfonyl,
- $(C_1-C_6)$-alkylsulfinyl,
- $(C_1-C_6)$-alkylthio,
- $(C_6-C_6)$-aryl,
- $(C_6-C_{14})$-aryl-$(C_1-C_6)$-alkyl or
- $(C_6-C_{14})$-aryloxy-$(C_1-C_6)$-alkyl, in which the aryl moiety can in each case be optionally substituted by one or two or three identical or different radicals selected from the group of the abovementioned preferred substituents of $(C_1-C_9)$-alkyl, b$_2$) - a radical of the formula VI, in which $R^{4a}$ is defined as $R^4$ in b$_1$) and W is —CO—, O— CO—, —SO$_2$—, —SO—, —S—, —NHCO—, —CH(OH)—;

b$_4$) - an amino protective group Fmoc, Z or Boc, $R^5$ and $R^7$ are hydrogen,
$R^6$ is - defined as $R^4$ and
$R^8$ is - hydrogen,
- hydroxyl,
- $(C_1-C_4)$-alkanoyloxy or
- $(C_1-C_8)$-alkyl.

3. The process for the preparation of compounds of the formula I as claimed in claim 1, wherein one of the radicals $R^2$ or $R^3$ is hydrogen.

4. The process for the preparation of compounds of the formula I as claimed in claim 1, wherein the compounds of the formula I have the SRRS-configuration or RSSR-configeration.

5. The process for the preparation of compounds of the formula I as claimed in claim 1, wherein $R^1$ is - a side-chain radical of the α-amino acids Ala, Val, Leu, Ile, Pro, Phe, Cha or Tyr, $R^2$ and $R^3$ are identical or different and are
a) - hydrogen
b) - a radical of the formula II in which
o and p=0,
n is 0 or 1 and
E is Ala, Val, Leu, Ile, Pro, Phe, Cha or Tyr;
D is $R^4$ or a radical of the formula IV where $R^4$ is $b_1$) - hydrogen,
- $(C_1-C_4)$ -alkyl,
- phenyl or naphthyl,
- phenylmethyl or naphthylmethyl, $b_2$) - is radical of the formula VI in which $R^{4a}$ is defined as in $b_1$) and W is —CO—, —O—CO—, —$SO_2$—, —SO—, —S—, —NHCO—, —CH(OH)—, or $b_4$) - an amino protective group Fmoc, Z or Boc, $R^5$, $R^7$ and $R^8$ are hydrogen, and $R^6$ is defined as $R^4$ in $b_1$).

6. The process for the preparation of compounds of the formula I as claimed in claim 1, wherein, for the preparation of a compound of the formula I in the SPuRS-configuration, a compound of the formula VII having the S-configuration is reacted at a temperature between room temperature and the boiling point of the reaction mixture.

7. The process for the preparation of compounds of the formula I as claimed in claim 1, wherein a compound of the formula VII is treated with the $NbCl_3$-dimethoxyethane complex in the presence of THF as solvent.

8. The process of claim 1, further comprising separating by crystallization the compound of the formula I.

* * * * *

UNITED STATES PATENT AND TRADEMARK OFFICE
CERTIFICATE OF CORRECTION

PATENT NO. : 5,463,124
DATED : October 31, 1995
INVENTOR(S) : Detlef JACOBI et al.

It is certified that error appears in the above-indentified patent and that said Letters Patent is hereby corrected as shown below:

Claim 1, Column 20, Line 46, "di- unsaturated" should read --diunsaturated--.

Claim 1, Column 20, Line 53, "$(C_1-C_7)$-alkanoyloxy" should read --$(C_1-C_8)$-alkanoyloxy--.

Claim 2, Column 24, Line 32, "$(C_6-C_6)$-aryl" should read --$(C_6-C_{14})$-aryl--.

Claim 4, Column 24, Lines 54 and 55, "configeration" should read --configuration--.

UNITED STATES PATENT AND TRADEMARK OFFICE
CERTIFICATE OF CORRECTION

PATENT NO. : 5,463,124
DATED : October 31, 1995
INVENTOR(S) : Detlef JACOBI et al It is certified that error appears in the above-indentified patent and that said Letters Patent is hereby corrected as shown below:

Claim 6, Column 26, Line 1, "SPuRS-configuration" should read --SRRS-configuration--.

Signed and Sealed this

Fifteenth Day of October, 1996

Attest:

BRUCE LEHMAN

Attesting Officer        Commissioner of Patents and Trademarks